(12) United States Patent
Buttimor

(10) Patent No.: US 8,669,210 B2
(45) Date of Patent: Mar. 11, 2014

(54) HIGH-STRENGTH, LOW VISCOSITY HERBICIDAL CONCENTRATE OF CLOPYRALID DIMETHYLAMIN

(75) Inventor: Robert M. Buttimor, New Plymouth (NZ)

(73) Assignee: Dow AgroSciences, LLC., Indianapolis, IN (US)

( * ) Notice: Subject to any disclaimer, the term of this patent is extended or adjusted under 35 U.S.C. 154(b) by 135 days.

(21) Appl. No.: 13/052,184

(22) Filed: Mar. 21, 2011

(65) Prior Publication Data

US 2011/0230349 A1   Sep. 22, 2011

Related U.S. Application Data

(60) Provisional application No. 61/316,003, filed on Mar. 22, 2010.

(51) Int. Cl.
| | |
|---|---|
| *A01N 43/40* | (2006.01) |
| *A61K 31/44* | (2006.01) |
| *C07D 213/79* | (2006.01) |
| *C07C 61/00* | (2006.01) |
| *C07C 61/08* | (2006.01) |
| *C07C 63/00* | (2006.01) |
| *C07C 65/00* | (2006.01) |
| *C07C 63/04* | (2006.01) |

(52) U.S. Cl.
USPC ........... 504/244; 504/260; 514/354; 546/326; 562/400; 562/405; 562/493

(58) Field of Classification Search
USPC ........... 504/244; 514/354; 546/326; 562/400; 562/405, 493
See application file for complete search history.

(56) References Cited

U.S. PATENT DOCUMENTS 6,297,197 B1 *  10/2001  Fields et al. .................. 504/260

FOREIGN PATENT DOCUMENTS

| CN | 101 326 912 A | 12/2008 |
|---|---|---|
| CN | 101326912 A | 12/2008 |

OTHER PUBLICATIONS

Specimen Label, Dow AgroSciences Lontrel® Turf and Ornamental Herbicide, effective date Jul. 25, 2007; Product Code: 69440; MSDS: 002805; Dow AgroSciences LLC, Indianapolis, IN 46268.

* cited by examiner

*Primary Examiner* — Jane C Oswecki
(74) *Attorney, Agent, or Firm* — Robert Chang

(57) ABSTRACT

This invention relates to a high-strength, aqueous herbicidal concentrate containing the clopyralid dimethylamine salt. The formulation is stable to storage and exhibits lower viscosity than other clopyralid amine salt formulations.

7 Claims, No Drawings

HIGH-STRENGTH, LOW VISCOSITY HERBICIDAL CONCENTRATE OF CLOPYRALID DIMETHYLAMIN

CROSS REFERENCE TO RELATED APPLICATIONS

This application claims the benefit of U.S. Provisional Application Ser. No. 61/316,003 filed on 22 Mar. 2010.

FIELD OF THE INVENTION

This invention concerns a high-strength, low viscosity aqueous concentrate of the herbicide clopyralid dimethylamine.

BACKGROUND OF THE INVENTION

Clopyralid, 3,6-dichloropicolinic acid, is an herbicide used to control broadleaf weeds in cereal crops, pasture, fallow, forest and industrial situations. Various formulations are currently marketed, many of which are aqueous solutions that are normally diluted prior to use. Typically the clopyralid is provided as an amine salt, which exhibits sufficiently high solubility in water to provide an aqueous concentrate herbicidal formulation (SL). Typical commercial formulations of clopyralid have an active loading of from about 300 grams acid equivalent per liter (gae/l) to about 450 gae/L of the monoethanolamine (MEA) or triisopropanolamine (TIPA) salts. Lontrel® herbicide (registered trademark of Dow AgroSciences LLC) is sold as a 360 gae/L SL formulation of the monoethanolamine salt of clopyralid in water and is used for the control of broadleaf weeds in turf and ornamentals.

High-strength formulations are desirable for a variety of economic and environmental reasons. For example, it is desirable to provide a high-strength concentrate in order to reduce shipping and handling costs and to reduce the amount of packaging material that must be disposed after use of the product. The high-strength concentrates should be stable and retain potency during storage and shipping. Furthermore, the high-strength concentrate should be a clear, homogeneous liquid that is stable at temperatures at least as high as 54° C. and should not exhibit any precipitation of solids at temperatures as low as −10° C.

There is a continuing need for new, high-strength SL herbicidal formulations that exhibit low viscosity and stability at low temperatures.

SUMMARY OF THE INVENTION

It has now been found that use of the dimethylamine (DMA) salt of clopyralid allows the preparation of a high-strength, aqueous concentrate of surprisingly low viscosity. More particularly, the present invention provides a high-strength herbicidal aqueous concentrate comprising: (a) water and (b) clopyralid, in the form of the DMA salt, in solution in the water in an amount of from about 450 grams of acid equivalent per liter (gae/l) to about 850 gae/L of the total composition.

In an effort to increase the active ingredient loading of an SL clopyralid formulation, it has been discovered that the DMA salt of clopyralid can create a physically stable concentrate containing greater than about 600 gae/L, preferably greater than about 750 gae/L, at −10° C. Furthermore, the concentrates produced from the clopyralid DMA salt have a much lower viscosity than other clopyralid amine salt SL formulations of lower concentration.

Aqueous concentrates of the commonly used amine salts of clopyralid can become increasingly viscous, particularly at lower temperatures, at concentrations of greater than about 400 gae/l, particularly at concentrations of greater than about 450 gae/l. The high viscosity makes the aqueous concentrates difficult to measure and pump, especially at lower temperatures that may be encountered at the beginning of the growing season.

In another embodiment, the present invention provides a method of treating plants with the herbicidal concentrate. The concentrate is typically applied to the plants post-emergently either as a concentrated solution or, preferably, as a more diluted solution with water.

DETAILED DESCRIPTION OF THE INVENTION

In general the present invention is directed to a high-strength aqueous herbicidal concentrate composition containing the DMA salt of clopyralid. More specifically, the present invention provides a high-strength herbicidal concentrate composition comprising: (a) water, and (b) clopyralid, in the form of the DMA salt, in solution in the water in an amount of from about 450 gae/l to about 850 gae/L of the total composition. In preferred embodiments, the high-strength herbicidal formulation includes greater than about 600 gae/l based upon the clopyralid acid equivalent of the clopyralid salt; more preferably, the high-strength herbicidal formulation includes greater than about 750 gae/l based upon the clopyralid acid equivalent of the clopyralid salt.

The present invention provides a high-strength herbicidal concentrate that is storage stable at high temperatures. That is, the concentrate forms a clear, homogeneous, stable solution that does not exhibit cloudiness under the storage conditions. More preferably, the concentrates of the present invention are stable at temperatures of greater than or equal to about 40° C., more preferably, at temperature equal to or greater than about 55° C.

Furthermore, the herbicidal concentrate also does not exhibit separation or precipitation (or crystallization) of any of the components at low temperatures. For example, the high-strength concentrate remains a clear solution at temperatures below about 0° C., more preferably at temperatures below about −5° C. and most preferably at a temperature equal to or less than about −10° C.

The high-strength herbicidal concentrates of the DMA salt of clopyralid are surprisingly less viscous than even less concentrated compositions of other salts of clopyralid. In preferred embodiments, the herbicidal concentrates of the present invention exhibit a viscosity of less than about 50 centipoise (50 mPa·s), even at temperatures as low as 5° C.

The concentrate described herein can be applied to plants in an amount sufficient to induce an herbicidal effect. For example, a concentrate prepared according to the present invention can be applied as a diluted aqueous solution to plants including the plants' leaves, stems, branches, flowers and/or fruit. The herbicidal formulation can be applied in an herbicidally effective amount sufficient to inhibit plant growth or kill individual plants.

The concentrate of the present invention may also be mixed with or applied with other herbicides. Suitable herbicides which may be mixed with or applied with the composition of the present invention to control plant growth include, but are not limited to, 2,4-D esters and amines, acetochlor, aclonifen, amidosulfuron, aminocyclopyrachlor, aminopyralid, aminotriazole, ammonium thiocyanate, asulam, atrazine, beflubutamid, benazolin, bentazone, bifenox, bromacil, bromoxynil, butachlor, butafenacil, butralin, butroxydim, carbetamide, carfentrazone, carfentrazone-ethyl, chlormequat, chlorsulfuron, chlortoluron, cinidon-ethyl, clethodim, clodinafop-propargyl, clomazone, clopyralid, cyanazine, cyclosulfamuron, cycloxydim, dicamba, dichlobenil, dichlorprop-P, diclofop-methyl, diflufenican, diflufenzopyr, dimefuron, dimethachlor, diquat, diuron, EPTC, ET-751, ethoxysulfuron, fenoxaprop, fenoxaprop-ethyl, fenoxaprop-ethyl+isoxidifen-ethyl, fenoxaprop-p-ethyl, flazasulfuron, florasulam, fluazifop, fluazifop-P-butyl, flucarbazone, flucetosulfuron (LGC-42153), flufenacet, flumetsulam, flumioxacin, flupyrsulfuron, fluroxypyr, fluroxypyr meptyl, flurtamone, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, iodosulfuron, iodosulfuron-ethyl-sodium, ioxynil, isoproturon, isoxaben, isoxaflutole, KIH-845, lactofen, linuron, MCPA, mecoprop-P, mesosulfuron, mesosulfuron-ethyl sodium, metazochlor, metosulam, metribuzin, metsulfuron, metsulfuron-methyl, MSMA, napropamide, norfurazon, orthosulfamuron, oryzalin, oxadiargyl, oxadiazon, oxyfluorfen, paraquat, pendimethalin, penoxsulam, picloram, picolinafen, pinoxaden, primisulfuron, profluazol, propaquizafop, propoxycarbazone, propyzamide, prosulfocarb, prosulfuron, pyraflufen ethyl, pyrasulfotole, pyribenzoxim (LGC-40863), pyroxsulam, quinmerac, quizalofop-ethyl-D, quizalofop-P-ethyl, quizalofop-p-tefuryl, sethoxydim, simazine, sulfentrazone, sulfosate, sulfosulfuron, tebuthiuron, tepraloxidim, terbacil, terbutryn, thiazopyr, thifensulfuron, thifensulfuron-methyl, topramezone, tralkoxydim, triasulfuron, tribenuron, tribenuron-methyl, triclopyr and trifluralin.

The herbicidal compositions prepared according to the present invention are highly effective against a variety of weeds. The concentrate of the present invention can be used as is or combined with other components including other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, wetting agents, spreading agents, dispersing agents, thickening agents, freeze point depressants, antimicrobial agents, crop oil, safeners and the like. The concentrated agricultural formulations are typically diluted in water and then applied by conventional means well known to those skilled in the art.

Example 1

Preparation of a High-Strength Clopyralid DMA Salt Formulation

A high-strength clopyralid DMA salt concentrate was prepared by reacting a mixture of clopyralid acid technical and water with just enough aqueous dimethylamine solution to neutralize the clopyralid. Following addition of the blue dye Hexaran Brilliant Blue Supra and dilution with water, a 600 gae/L formulation of the clopyralid DMA salt was obtained. The example described in Table 1 demonstrates the invention.

TABLE 1

Clopyralid DMA 600 gae/L Formulation

| Component | Role | AI | AI (wt %) | AE |
|---|---|---|---|---|
| clopyralid | active ingredient | 600 g/L | 49.18% w/w | 600 g/L |
| Hexaran Brilliant | color dye | 0.25 g/L | 0.02% w/w | |

TABLE 1-continued

Clopyralid DMA 600 gae/L Formulation

| Component | Role | AI | AI (wt %) | AE |
|---|---|---|---|---|
| Blue Supra | | | | |
| dimethylamine | neutralizer | 140.94 g/L | 11.55% w/w | |
| water | solvent | 478.81 g/L | 39.25% w/w | |

Example 2

Viscosity of High-Strength Clopyralid DMA Salt Formulation

The viscosity of sample formulations was measured with a TA Instruments AR 2000 rheometer. Table 2 lists the viscosity measured for the concentrate described in Example 1 and compares it to a commercial clopyralid TIPA 300 gae/L formulation (Dow AgroSciences Australia Ltd.) over a temperature range of 5 to 25° C. The viscosity of the high-strength clopyralid DMA salt concentrate was significantly lower than the clopyralid TIPA commercial concentrate, particularly at the lower temperatures.

TABLE 2

Comparison of the Viscosities of Clopyralid DMA 600 gae/L and Clopyralid TIPA 300 gae/L Concentrates at 5 to 25° C.

| | Viscosity (mPa · s) | |
|---|---|---|
| Temperature ° C. | clopyralid DMA (600 gae/L) | clopyralid TIPA (300 gae/L) |
| 5 | 33 | 50 |
| 10 | 29 | 37 |
| 15 | 22 | 28 |
| 20 | 18 | 21 |
| 25 | 15 | 17 |

Example 3

Stability of High-Strength Clopyralid DMA Salt Concentrates to Low Temperature

Several crystallization studies have been conducted on the high-strength clopyralid DMA concentrates using several sources of active ingredient. Three batches of clopyralid technical from two sources were converted into high-strength clopyralid DMA sample concentrates and these were seeded with active ingredient crystals and stored for 6 days at −10° C. All samples remained physically stable (no crystallization) and were clear, homogeneous liquids. The concentrations of these samples ranged from 783 gae/L to 850 gae/L of clopyralid DMA.

Example 4

Herbicidal Efficacy of High-Strength Clopyralid DMA Salt Concentrate

The high-strength clopyralid DMA salt concentrate was evaluated for efficacy against capeweed (AROCA) in field trials. Table 3 shows the biological efficacy of the 630 gae/l clopyralid DMA salt concentrate compared to a commercial concentrate of Lontrel® Herbicide containing clopyralid TIPA salt at a concentration of 300 gae/L. Across all application rates the high-strength clopyralid DMA salt concentrate showed nearly equivalent performance to the commercial clopyralid TIPA salt formulation.

TABLE 3

Comparison of High-Strength Clopyralid DMA (630 gae/L) and Lontrel ® Herbicide (clopyralid TIPA 300 gae/L) at Equivalent Rates for Control of Capeweed (AROCA)

| Treatment | Formulation Concentration (gae/L) | Application Rate (gae/ha) | % Control of Capeweed* |
|---|---|---|---|
| clopyralid DMA | 630 | 22 | 67 |
| clopyralid TIPA | 300 | 22 | 63 |
| clopyralid DMA | 630 | 43 | 87 |
| clopyralid TIPA | 300 | 45 | 84 |
| clopyralid DMA | 630 | 86 | 94 |
| clopyralid TIPA | 300 | 90 | 91 |
| clopyralid DMA | 630 | 180 | 99 |
| clopyralid TIPA | 300 | 180 | 98 |

*average of six trials
AROCA *Arctotheca calendula* capeweed

What is claimed is:

1. A high-strength herbicidal aqueous concentrate comprising: (a) water and (b) clopyralid dimethylamine, in solution in the water, wherein the concentrate contains 600 gae/L to 850 gae/L of the clopyralid dimethylamine.

2. The concentrate of claim 1 having a viscosity less than about 50 centipoise at 5° C.

3. A method of controlling undesirable vegetation which comprises applying to the vegetation a water-diluted composition of claim 1.

4. A composition comprising:
 (a) water;
 (b) clopyralid;
 (c) dimethylamine;
 wherein said clopyralid and said dimethylamine are dissolved in the water; and
 wherein said clopyralid is provided in the composition in an amount from 600 to 850 gae/L of the composition.

5. The composition of claim 4 wherein said clopyralid is provided in the composition in an amount of 630 gae/L of the composition.

6. The composition of claim 4 wherein said clopyralid is provided in the composition in an amount of from 783 to 850 gae/L of the composition.

7. The concentrate of claim 4 that remains a clear solution at 0° C., has a viscosity less than about 50 centipoise at 5° C., and is stable at 40° C.

* * * * *